(12) United States Patent
Beck et al.

(10) Patent No.: US 11,273,005 B2
(45) Date of Patent: Mar. 15, 2022

(54) MEDICAL ASSET TRACKING METHODS AND APPARATUS

(71) Applicant: SENOPS TRACKER, Pleasantville, NY (US)

(72) Inventors: Christopher J. Beck, Pleasantville, NY (US); G. Michael Wright, Ramsey, NJ (US); Michael R. Bielski, Manorville, NY (US); Michael Calamita, Hampton Bays, NY (US); James Patrick Lanzilotta, Sr., Northport, NY (US); Timothy Joseph Relihan, Lake Worth, FL (US); James Clinton Wightman, II, Saint James, NY (US)

(73) Assignee: SENOPS TRACKER, Pleasantville, NY (US)

( * ) Notice: Subject to any disclaimer, the term of this patent is extended or adjusted under 35 U.S.C. 154(b) by 0 days.

(21) Appl. No.: 16/789,695

(22) Filed: Feb. 13, 2020

(65) Prior Publication Data

US 2020/0261183 A1   Aug. 20, 2020

Related U.S. Application Data

(60) Provisional application No. 62/807,540, filed on Feb. 19, 2019.

(51) Int. Cl.
*A61B 90/98* (2016.01)
*H01L 41/04* (2006.01)
(Continued)

(52) U.S. Cl.
CPC .............. *A61B 90/98* (2016.02); *G06F 3/16* (2013.01); *H01L 41/042* (2013.01);
(Continued)

(58) Field of Classification Search
CPC ......... H04W 4/02; H04W 4/80; H04W 4/021; H04W 4/027; H04W 4/029;
(Continued)

(56) References Cited

U.S. PATENT DOCUMENTS

| 6,255,949 B1 | 7/2001 | Nicholson et al. |
| 6,717,516 B2 | 4/2004 | Bridgelall |

(Continued)

OTHER PUBLICATIONS

International Search Report dated May 11, 2020.

*Primary Examiner* — Quan Zhen Wang
*Assistant Examiner* — Mancil Littlejohn, Jr.
(74) *Attorney, Agent, or Firm* — Hoffmann & Baron, LLP

(57) ABSTRACT

An apparatus for tracking surgical assets includes a processor, a power supply for providing power to an entirety of circuitry of the apparatus, and a communications engine coupled with the processor. The communications engine is configured to communicate with one or more mobile devices external to the apparatus. The tracking apparatus further includes a piezoelectric element for generating an audible indication in response to an activation signal supplied thereto, and a piezoelectric driver coupled with the piezoelectric element and the processor. The piezoelectric element is disposed on an exterior surface of the apparatus. The piezoelectric driver is configured to generate the activation signal supplied to the piezoelectric element as a function of a user-initiated request signal and/or a control signal generated by the processor. The tracking apparatus is adapted to withstand elevated temperatures during a sterilization process of a medical asset to which the apparatus is attached.

18 Claims, 4 Drawing Sheets

(51) Int. Cl.
  *H04W 4/021* (2018.01)
  *H04W 84/12* (2009.01)
  *H04W 4/80* (2018.01)
  *G06F 3/16* (2006.01)
  *H04W 4/029* (2018.01)

(52) U.S. Cl.
  CPC ........... *H04W 4/021* (2013.01); *H04W 4/029* (2018.02); *H04W 4/80* (2018.02); *H04W 84/12* (2013.01)

(58) Field of Classification Search
  CPC . H01L 41/0973; H01L 41/042; H01L 41/053; G06F 3/16; A61B 90/98
  See application file for complete search history.

(56) References Cited

U.S. PATENT DOCUMENTS

| | | | |
|---|---|---|---|
| 7,118,029 B2 | 10/2006 | Nycz et al. | |
| 7,518,502 B2 | 4/2009 | Austin et al. | |
| 7,636,046 B2 | 12/2009 | Caliri et al. | |
| 7,701,334 B1* | 4/2010 | Perkins | G16H 40/20 340/539.13 |
| 7,868,754 B2 | 1/2011 | Salvat, Jr. | |
| 8,089,062 B2 | 1/2012 | Wu et al. | |
| 8,248,242 B2 | 8/2012 | Caliri et al. | |
| 10,070,309 B2* | 9/2018 | Patterson | H04W 48/02 |
| 10,580,281 B2* | 3/2020 | Daoura | G08B 21/0277 |
| 2005/0027323 A1 | 2/2005 | Mulligan et al. | |
| 2005/0061076 A1 | 3/2005 | Kim | |
| 2005/0134452 A1 | 6/2005 | Smith | |
| 2005/0249049 A1* | 11/2005 | Jarrett | G08B 15/004 368/250 |
| 2008/0030345 A1* | 2/2008 | Austin | A61B 90/98 340/572.8 |
| 2014/0365615 A1 | 12/2014 | Fernandes | |
| 2015/0088538 A1 | 3/2015 | Dykes et al. | |
| 2015/0165466 A1* | 6/2015 | Hammer | B05B 17/0615 239/102.2 |
| 2018/0000556 A1* | 1/2018 | Blair | A61B 90/98 |

* cited by examiner

MEDICAL ASSET TRACKING METHODS AND APPARATUS

CROSS-REFERENCE TO RELATED APPLICATIONS

This application claims priority to U.S. Provisional Patent Application No. 62/807,540 filed Feb. 19, 2019 entitled "Medical Asset Tracking Methods and Apparatus," the disclosure of which is incorporated by reference herein in its entirety for all purposes.

BACKGROUND OF THE INVENTION

The present invention relates generally to the electrical, electronic and computer arts, and, more particularly, to methods and apparatus for tracking medical assets.

The ability to rapidly determine the location of objects located within a facility is becoming increasingly vital, particular when the objects to be located are medical assets within a hospital or other medical facility. Not only does the ability to track the location of objects within a facility increase efficiency, but it also decreases the likelihood of medical emergencies in the context of medical asset tracking. Specifically, in a typical hospital there can be numerous shifts of doctors and related medical staff utilizing the same equipment. When a new shift arrives, the ability to quickly locate medical equipment not only results in a more efficient use of resources, but can also result in averting a medical emergency.

Conventionally, in medical asset tracking applications, passive identification tags, such as radio frequency identification (RFID) tags, are attached to medical assets. When interrogated by a remote transponder, these RFID tags will broadcast their unique identification information to the transponder. Unfortunately, however, RFID tags must reside in close proximity to the transponder to operate, and thus the ability to identify objects over a large area is significantly restricted. Furthermore, most RFID tags are incapable of transmitting location information, which requires a global positioning system (GPS) or other location engine embedded therein; RFID tags are generally employed for object identification rather than object location.

There are some known methods for monitoring the location of objects which involve attaching a tracking device (e.g., a GPS-enabled RFID tag) to the object being tracked and using a GPS feature to report the location of the tracking device, and hence the location of the object. However, if the tracking device cannot communicate with GPS satellites, such as when they reside within a building, as they often will, their location cannot be determined.

Furthermore, in a medical environment, most known asset tracking mechanisms are incapable of surviving the extreme temperatures typically used for sterilization of medical assets (e.g., autoclaving). Medical asset sterilization generally requires subjecting a medical instrument or other medical asset to temperatures in excess of 120 degrees Fahrenheit (° F.), and as high as about 300° F., to destroy pathogens (e.g., bacteria, viruses, etc.). These extreme temperatures are generally beyond the maximum specified operating range of most RFID tags or similar wireless tracking devices.

BRIEF SUMMARY OF THE INVENTION

The present invention, as manifested in one or more embodiments, includes a method, apparatus and system for tracking medical assets (e.g., medical trays, surgical instruments and related equipment), for example in a medical facility. An apparatus for tracking medical assets according to an embodiment of the invention can identify medical assets through GPS-enabled capabilities and, in one or more embodiments, is adapted to audibly broadcast its location, which is advantageous in determining the location of multiple medical assets residing in the same large space. In some embodiments, the apparatus includes a location engine (e.g., GPS-enabled) configured to provide a location of the apparatus. Moreover, an apparatus for tracking medical assets according to an embodiment of the invention is beneficially adapted to survive sterilization temperatures which would otherwise damage conventional tracking devices.

In accordance with one embodiment of the invention, an apparatus for tracking surgical assets includes at least one processor, a power supply for providing power to an entirety of circuitry of the apparatus, and a communications engine coupled with the processor. The communications engine is configured to establish communications with one or more mobile devices external to the apparatus. The tracking apparatus further includes a piezoelectric element for generating an audible indication in response to an activation signal supplied thereto, and a piezoelectric driver coupled with the piezoelectric element and the processor. The piezoelectric element is disposed on an exterior surface of the apparatus. The piezoelectric driver is configured to generate the activation signal supplied to the piezoelectric element. The tracking apparatus is adapted to withstand elevated temperatures to which the apparatus may be exposed, such as, for example, during a sterilization process (e.g., autoclaving) of a medical asset to which the apparatus is attached.

In accordance with another embodiment of the invention, a method for tracking a medical asset includes attaching a tracking device to the medical asset being tracked. The tracking device includes at least one processor, a power supply for providing power to an entirety of circuitry of the apparatus, a communications engine coupled with the processor, a piezoelectric element disposed on an exterior surface of the tracking device for generating an audible indication in response to an activation signal supplied thereto, and a piezoelectric driver coupled with the piezoelectric element and the processor, the piezoelectric driver being configured to generate the activation signal supplied to the piezoelectric element as a function of a control signal. The method further includes sending, by a user attempting to locate the medical asset, a request signal, whereby receiving the request signal by the communications engine causes the processor to generate the control signal for activating the piezoelectric element to generate the audible indication for assisting the user in locating the medical asset to which the tracking device is attached.

As may be used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software and/or software module(s) stored in a computer readable storage medium (or multiple such media) and implemented on a hardware processor, or (iii) a combination of (i) and (ii); any of (i)-(iii) implement the specific techniques set forth herein.

Techniques according to embodiments of the present invention can provide substantial beneficial technical effects. By way of example only and without limitation, one or more embodiments of the invention provide techniques for tracking medical assets in, for example, a medical facility (or, indeed, anywhere) having one or more of the following advantages, among other benefits:

- an ability to audibly broadcast a location of a medical asset in a large room;
- an ability to endure the extreme temperatures and pressures of medical asset sterilization (e.g., autoclaving) without damage;
- an ability to provide GPS-enabled Web-based location information anywhere an LTE (Long Term Evolution) infrastructure is present;
- an unattended battery life of 1-2 years, dependent on use case.

These and other features and advantages of the present invention will become apparent from the following detailed description of illustrative embodiments thereof, which is to be read in connection with the accompanying drawings.

BRIEF DESCRIPTION OF THE SEVERAL VIEWS OF THE DRAWING

The following drawings are presented by way of example only and without limitation, wherein like reference numerals (when used) indicate corresponding elements throughout the several views, and wherein.

It is to be appreciated that elements in the figures are illustrated for simplicity and clarity. Common but well-understood elements that may be useful or necessary in a commercially feasible embodiment may not be shown in order to facilitate a less hindered view of the illustrated embodiments.

DETAILED DESCRIPTION OF PREFERRED EMBODIMENTS

Principles of the present invention will be described herein in the context of illustrative apparatus, systems and methods for tracking surgical assets, such as, for example, medical trays, surgical instruments and related surgical components and equipment, in a medical facility or other space, such as a hospital. It is to be appreciated, however, that the invention is not limited to the specific apparatus, systems and/or methods illustratively shown and described herein. Rather, it will become apparent to those skilled in the art given the teachings herein that numerous modifications can be made to the embodiments shown that are within the scope of the claimed invention. That is, no limitations with respect to the embodiments shown and described herein are intended or should be inferred.

Many medical procedures involve the use of specialized surgical instruments and medical devices, which are generally assembled together and placed in surgical trays. These surgical trays must be available when the surgeon is scheduled to perform the operation, and the inability to locate a given tray(s) can result in delaying the scheduled surgery, which in turn increases costs to the surgeon and medical facility, and may even endanger patient care to the extent a surgical success requires timely performance. Consequently, the ability to quickly determine the location of a particular medical asset, even in a large room within the medical facility, is desirable.

Aspects according to embodiments of the invention provide an apparatus, system and method for quickly determining the location of medical assets (e.g., medical trays, surgical instruments and related equipment) in a medical facility or other space. More particularly, in addition to including a location engine (e.g., GPS module) for providing precise absolute location coordinates of the apparatus, where GPS satellite reception is available, an apparatus according to an embodiment of the invention is adapted to audibly broadcast its location, either on its own or in response to a user-initiated request, which is advantageous when attempting to determine the location of multiple medical assets residing in the same space (e.g., large storage room). Moreover, the apparatus for tracking medical assets according to one or more embodiments of the invention is adapted to survive the extreme temperatures of pathogen sterilization without damaging the tracking apparatus.

Figure 1:
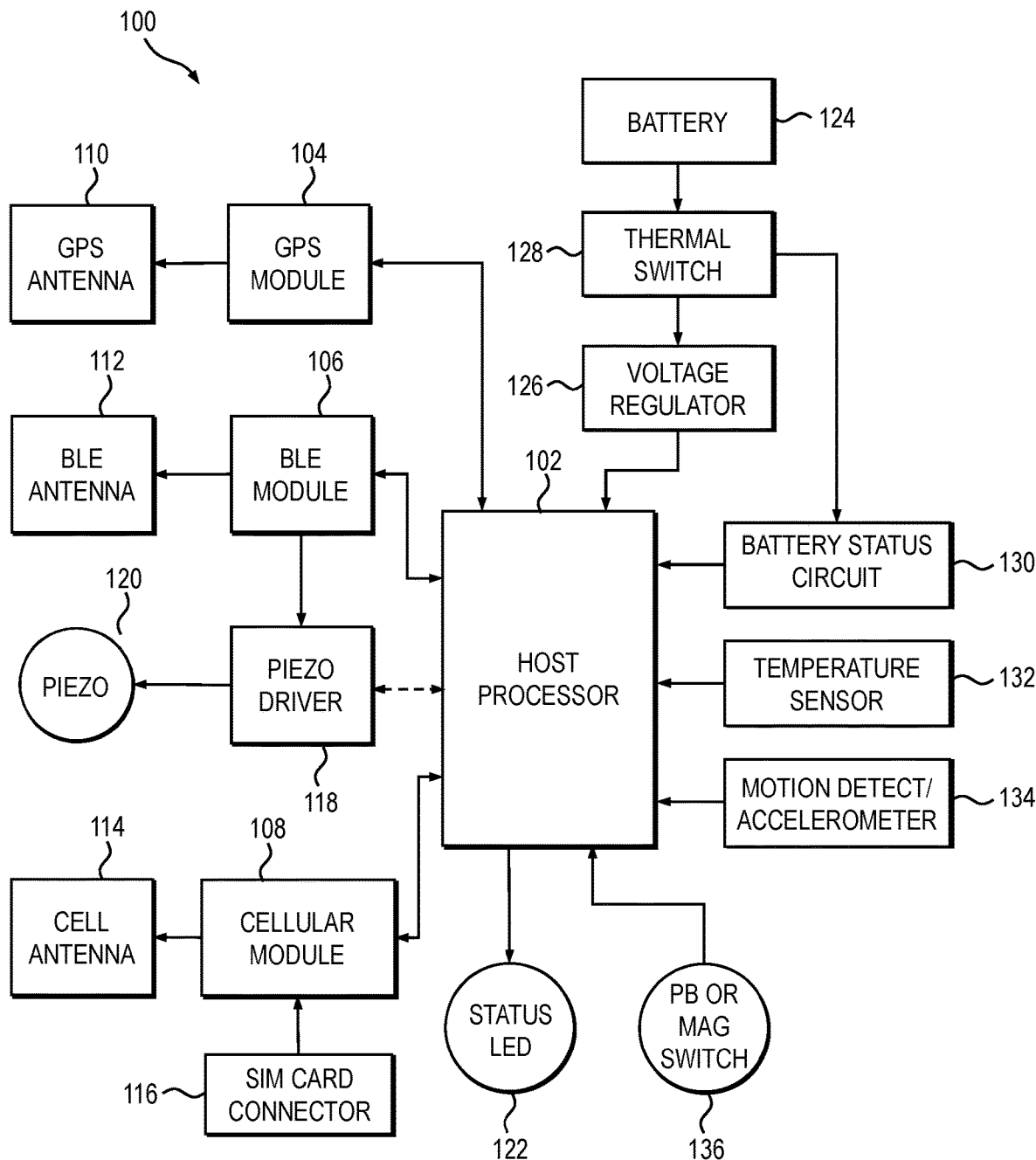
FIG. 1 is a block diagram depicting at least a portion of an exemplary tracking apparatus or system for locating a medical asset to which the apparatus/system is attached, in accordance with an embodiment of the present invention.

FIG. 1 is a block diagram conceptually depicting at least a portion of an exemplary tracking apparatus (or system) 100 for locating a medical asset to which the apparatus is attached, according to an embodiment of the invention. In applications wherein the tracking apparatus 100 is used to determine the location of a medical asset, such as, for example, a surgical tray, the tracking apparatus is preferably sized and adapted for attachment to an exterior of the surgical tray. In this regard, however, it is to be appreciated that embodiments of the invention are not limited to any particular shape and/or dimensions for the tracking apparatus 100.

The exemplary tracking apparatus 100 includes a host processor 102 configured to monitor and control one or more functions of the apparatus, and to communicate with a user or with other devices, either via a wired or wireless connection, for performing certain actions and/or conveying certain information. Although depicted conceptually as a single component, the host processor 102 may, in one or more embodiments, comprise a plurality of processors, with each processor performing one or more actions (or a portion thereof) of the tracking apparatus 100. The tracking apparatus 100 further preferably includes one or more communication modules, such as, for example, a GPS module or receiver 104, a Bluetooth Low Energy (BLE) module or transceiver 106 and a cellular module or transceiver 108 (e.g., Long-term Evolution (LTE) CAT M1, fifth generation (5G), etc.), all in operative communication with the host processor 102. The host processor 102 may use one or more of these communications modules 104, 106, 108 for communicating with other devices external to the tracking apparatus 100, such as, for example, a mobile device of a user.

The GPS module 104 is coupled with a GPS antenna 110. The GPS module 104 includes circuitry adapted to receive GPS satellite signals from the GPS antenna 110 and to generate positional coordinates for providing a precise location of the apparatus 100 to the host processor 102 when GPS satellite reception is available.

The BLE module 106 is coupled with a BLE antenna 112. The BLE module 106 includes circuitry adapted to establish a wireless personal area network (WPAN) for communicating with other Bluetooth-enabled devices using a Bluetooth communications protocol. Mobile operating systems, including iOS, Android, Windows Phone and BlackBerry, as well as macOS, Linux, Windows 8 and Windows 10, natively support BLE.

The cellular module 108 is coupled with a cellular antenna 114 for providing long-range wireless communications with other mobile devices and the like. In one or more embodiments, the cellular antenna 114 comprises an LTE antenna. As is well known by those skilled in the relevant art, LTE is a standard for high-speed wireless communication for mobile devices and data terminals, based on the Global System for Mobile communications (GSM)/Enhanced Data rates for GSM Evolution (EDGE) and Universal Mobile Telecommunications System (UMTS)/High Speed Packet Access (HSPA) technologies. It is to be appreciated, however, that embodiments of the invention are not limited to an LTE cellular protocol; rather, other cellular protocols, such as, for example, 5G, are similarly contemplated. The cellular module 108 may be operatively coupled with a subscriber identity module (SIM) card connector 116 through which configuration data and the like is stored for communicating with a carrier.

In order to provide an audible indication feature, the tracking apparatus 100 further includes a piezoelectric (hereinafter "piezo") driver 118 connected with a piezo element 120. The piezo driver 118, in one or more embodiments, comprises an oscillator circuit configured to generate an output signal for vibrating the piezo element 120 at a prescribed frequency to thereby produce sound. In the exemplary embodiment shown in FIG. 1, the piezo driver 118 is coupled with the BLE module 106 and is selectively activated by an enable signal received from the BLE module. Alternatively, in one or more embodiments, the piezo driver 118 is coupled directly with the host processor 102, and the host processor may be configured to generate an enable signal for activating the piezo element 120.

In one or more embodiments, the piezo driver 118 is configured to vary one or more characteristics of the audible indication. For example, the piezo driver 118 may vary a frequency and/or pattern of audio emanating from the piezo element 120 to thereby uniquely distinguish the tracking apparatus 100 from other tracking devices located in the same vicinity. For instance, a user who is tracking multiple assets may set one tracking device to a first frequency (e.g., 1 KHz) and a second tracking apparatus to a second frequency (e.g., 4 KHz), or set the second tracking apparatus to produce a certain pattern of tones (e.g., two short tone bursts followed by a gap in a repeating sequence). In one or more embodiments, a user can control one or more parameters of the audible indication, preferably using an application program running on a mobile device or the like. This feature may be added or modified with a software update, as will become apparent to those skilled in the art.

By way of example only and without limitation, a user may send a request, via a BLE-enabled wireless mobile device (e.g., mobile phone, etc.), for the tracking apparatus 100 to audibly broadcast its location. The BLE module 106 receives the user request through the BLE antenna 112 and transmits this request to the host processor 102, which then instructs the BLE module to activate the piezo driver 118 to produce an audible indication to help the user locate the tracking apparatus 100. Alternatively, in one or more embodiments, the host processor 102 may directly activate the piezo driver 118 (without signaling the BLE module 106) to cause the piezo driver 118 to produce an audible indication. This may be beneficial when the tracking apparatus is configured to audibly broadcast its presence at periodic intervals, without the need for user interaction.

The tracking apparatus 100, in one or more embodiments, may optionally include a visual indication feature in addition to the audible indication feature. To implement this visual indication feature, the tracking apparatus 100 includes a visual indicator 122, which may comprise a status light emitting diode (LED), operatively coupled with the host processor 102. Hence, when requested (e.g., in response to a user-initiated command or otherwise) to provide a visual indication of its presence, the tracking apparatus 100 is configured to supply an appropriate output signal, such as from the host processor 102, for turning on the status LED 122.

As previously stated, the tracking apparatus is preferably designed to withstand the extreme temperatures and pressures of sterilization, such as autoclaving. In order to accomplish this, the piezo element 120 is preferably formed of a ceramic piezoelectric material with electrically conductive electrodes (e.g., brass, copper, etc.), although other materials capable of demonstrating a piezoelectric effect while withstanding elevated temperatures (e.g., greater than about 120° F. for a prescribed period of time) without damage are similarly contemplated, according to embodiments of the invention.

The tracking apparatus 100, being adapted for portability, preferably includes a power supply 124, or other long-term energy storage element (e.g., battery), for powering the various circuits and modules in the tracking apparatus. In some embodiments, the power supply 124 may comprise a rechargeable battery. In this instance, additional circuitry may be included (e.g., incorporated into the power supply 124) for charging the battery and monitoring battery charge. In one or more embodiments, a wireless charging circuit (e.g., using inductive, such as near-field communication (NFC), or resonant charging) is used so as not to compromise the sealing of the tracking apparatus enclosure. In this instance, wireless charging circuitry may be integrated within the power supply 124.

Preferably, the power supply 124 is designed to have an extended operating life (e.g., greater than about three years) without the need for replacement. Of course, battery life is highly dependent on use case. For example, reporting periods of the GPS module 104, cellular connection and BLE/audible alarm actuation frequency, as well as environmental factors such as network availability and temperature, will determine actual battery life. Given a baseline reporting period of twice per day, the expected battery life is greater than one year but less than two years. In one or more embodiments, the power supply 124 in the tracking apparatus 100 is not replaceable, and therefore once the operating life is complete, the tracking apparatus would require replacement.

Furthermore, the power supply 124 is preferably adapted to withstand the extreme temperatures of sterilization (e.g., greater than about 120° F. for a prescribed period of time). For example, in one or more embodiments, four type AA Tadiran lithium primary cells, model TLH-5903 (commercially available from Tadiran U.S. Battery Division, Lake Success, N.Y.), are connected in a two-series, two-parallel (2×2) configuration. Each of these battery cells has a rated capacity of 2,000 milliamp-hours (mA·h), and a temperature rating of 125 degrees Celsius (° C.) operational and 150° C. storage.

In order to provide a substantially constant voltage output level as well as power conditioning for its internal circuitry, the tracking apparatus 100 may include a voltage regulator 126 connected in series between the power supply 124 and the host processor 102 and other functional circuits/modules. The voltage regulator 126 is designed to automatically maintain a constant output voltage level despite variations in the input voltage level supplied to the voltage regulator. Various circuit architectures may be used to implement the voltage regulator. For instance, the voltage regulator 126 may utilize a simple feed-forward design, or it may include negative feedback. Moreover, the voltage regulator 126 may be adapted to output multiple regulated DC voltages, depending upon the design and functionality of the circuitry within the tracking apparatus 100, as will become apparent to those skilled in the art.

When undergoing a high-temperature sterilization process, the tracking apparatus 100 is preferably disabled. This may be accomplished, in one or more embodiments, by including a thermally activated switch (i.e., thermal switch) 128 connected in series between the power supply 124 and the voltage regulator 126. The thermal switch 128, in one or more embodiments, comprises a bimetallic element that is temperature responsive and is configured to deactivate the power supply 124 to the entirety of the circuitry in the tracking apparatus 100 when an internal temperature of the tracking apparatus 100 in which the thermal switch resides exceeds a prescribed threshold value (e.g., 80° C.). In operation, the bimetallic element in the thermal switch 128 may include hysteresis, such that the switch mechanically opens (thereby electrically disconnecting the power supply 124 to the entirety of circuitry in the tracking apparatus 100) when the temperature exceeds a first threshold (e.g., 80° C.), and mechanically closes (thereby electrically reconnecting the power supply 124 to the entirety of circuitry in the tracking apparatus 100) when the temperature drops below a second threshold value consistent with an acceptable operating temperature range (e.g., 50° C.).

The tracking apparatus 100, in one or more embodiments, may optionally include other functional circuitry for providing corresponding information to the host processor 102. By way of illustration only and without limitation, the tracking apparatus 100 preferably includes a battery status circuit 130, a temperature sensor 132 and a motion detector/accelerometer 134. The battery status circuit 130 is coupled with the power supply 124, through the thermal switch 128, and the host processor 102. The battery status circuit 130 is preferably adapted to obtain information regarding an operational status of the power supply (e.g., voltage level) and to provide such information to the host processor. The host processor 102 may use this information to take one or more actions in response thereto, such as to shut down certain non-essential circuitry when the battery voltage falls below a prescribed threshold level. Likewise, the temperature sensor 132 is preferably configured to provide temperature information to the host processor 102, and the motion detector 134 is configured to provide information to the host processor regarding a position or motion of the tracking apparatus 100. The host processor 102 may then take one or more actions in response to this temperature and motion information, such as, for example, placing one or more circuits into a "sleep" mode when no motion is sensed by the motion detector 134 for a prescribed period of time.

The tracking apparatus may further optionally include a pushbutton (PB) or magnetic (MAG) switch 136 operatively coupled with the host processor 102. In one or more embodiments, a magnetic switch is used so as not to compromise the integrity of the enclosure. The host processor 102, in one or more embodiments, is configured to receive a signal generated by the magnetic switch 136 and perform one or more action as a function thereof. For example, a function of the magnetic switch 136 may be to enable and/or reset the tracking apparatus 100.

Figure 2A:
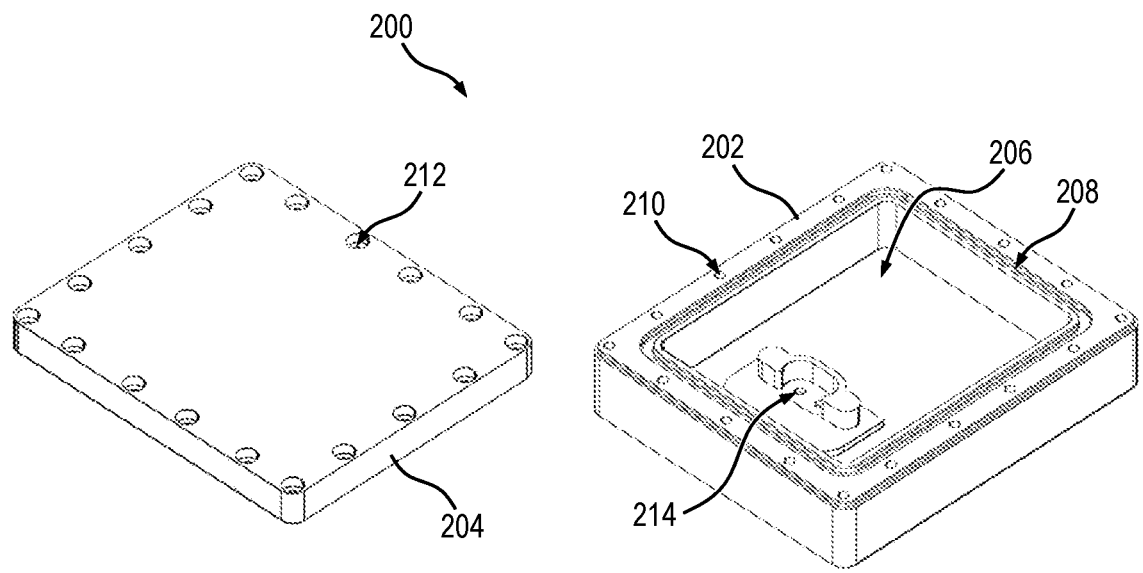
FIGS. 2A and 2B are perspective views depicting at least a portion of an exemplary enclosure adapted for housing circuitry of the tracking apparatus, according to an embodiment of the present invention.
Figure 2B:
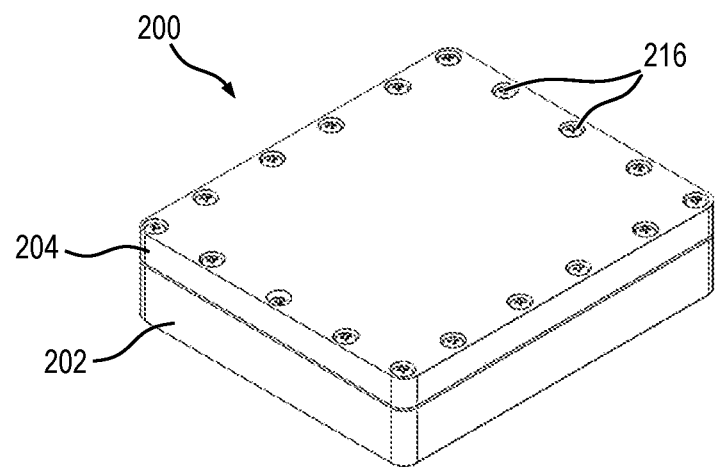

As previously stated, the tracking apparatus 100 is beneficially able to endure the extreme temperatures of a sterilization environment (e.g., autoclaving process). Consequently, one or more embodiments of the invention provide a hermetically sealed enclosure within which critical circuitry of the tracking apparatus is disposed. Turning now to FIGS. 2A and 2B, an exemplary enclosure 200 according to an embodiment of the invention is shown in perspective view. With reference to FIG. 2A, the exemplary enclosure 200 includes a main housing 202 and a separate housing cover 204 configured for engagement with the main housing. The main housing 202, in one or more embodiments, is shaped having a substantially rectangular footprint, with a bottom and vertical sidewalls of the main housing defining an interior space 206 adapted to contain circuitry of the tracking apparatus (e.g., 100 in FIG. 1) therein. As previously stated, however, embodiments of the invention are not limited to any particular shape and/or dimensions for the main housing 202.

The main housing 202 preferably includes a channel 208, or other depression (e.g., groove or trench), formed in the sidewalls surrounding an upper surface of a periphery of the interior space 206. In one or more embodiments, the channel 208 is adapted to receive an O-ring, gasket, or other sealing element (e.g., gasket 302 shown in FIG. 3A). Although not explicitly shown in FIG. 2A, an underside of the housing cover 204 preferably includes a rib, which extends slightly from the underside surface of the housing cover, and is configured to align with the channel 208 in the main housing. When the housing cover 204 is placed over the main housing 202, the rib helps to compress the O-ring into the corresponding channel 208 thereby hermetically sealing the enclosure 200. Other arrangements for sealing the cover 204 with the main housing 202 are similarly contemplated, as will become apparent to those skilled in the art.

For example, in one or more alternative embodiments, rather than using a rib to compress the O-ring into the underlying channel 208, the housing cover 204 may also include a channel in the underside surface which is aligned with the channel in the main housing. In this alternative configuration, the O-ring is designed to be of an appropriate thickness such that when placed in the channel 208 of the main housing 202, at a least a portion of the O-ring extends above an upper surface of the main housing. The portion of the O-ring extending above the main housing 202 is adapted to fit tightly into the corresponding channel in the housing cover 204, so that when placed on the main housing 202, the O-ring allows the housing cover 204 to be hermetically sealed with the main housing.

The enclosure 200, particularly the main housing 202 and housing cover 204, is preferably formed of a substantially rigid material that will not deform under sterilization temperatures (e.g., up to about 150° C.) and pressures (e.g., about 300 kilopascals (kPa) for an Autoclaving profile). In one or more embodiments, the main housing 202 and housing cover 204 comprise a thermoplastic polyetherimide high heat polymer material, such as, but not limited to, ULTEM® 1000 (a registered trademark of SABIC Global Technologies B.V). It is to be understood that embodiments of the invention are not limited to any specific material(s) used to form the enclosure 200. For example, a ceramic main housing 202 and/or housing cover 204 may be used. It is to be appreciated that the main housing 202 and housing cover 204 need not be formed of the same material. Moreover, although the enclosure 200, in one or more embodiments, is sized to be about four inches in length, about four inches in width, and about one inch in height, embodiments of the invention are not limited to any specific dimensions for the enclosure.

The main housing 202 further includes a plurality of openings 210 formed vertically through the sidewalls of the main housing that are aligned with corresponding openings 212 through the housing cover 204. Screws, bolts or other fasteners may be placed through these openings 210, 212 to secure the housing cover 204 to the main housing 202. Although embodiments of the invention are not limited to any particular number of fasteners used to secure the housing cover 204 to the main housing 202, an appropriate number of fasteners (e.g., at least one in each corner) are employed so that a hermetic seal can be formed between the main housing and housing cover to thereby prevent intrusion of air and moisture.

With continued reference to FIG. 2A, the main housing 202 includes openings 214 through which conductors are passed for electrically connecting circuitry of the tracking apparatus (e.g., piezo driver 118 in FIG. 1) with the piezo element (e.g., 120 in FIG. 1). As will be explained in further detail in conjunction with FIGS. 3A and 3B, rather than having the piezo element disposed on an interior of the enclosure 200 where a volume of sound emanating therefrom would be substantially attenuated, the piezo element, in one or more embodiments, is advantageously disposed on an exterior surface of the enclosure (e.g., a back surface of the main housing 202) so as not to diminish the volume of sound produced by the piezo element. Accordingly, since the conductors pass through the openings 214 for electrically connecting circuitry of the tracking apparatus, disposed in the interior of the main housing, with the piezo element, disposed on the exterior of the main housing 202, they may be referred to herein as signal feedthroughs.

FIG. 2B depicts the exemplary enclosure 200 with the housing cover 204 secured to the main housing 202 using a plurality of bolts 216 through corresponding openings 210 and 212 in the main housing and housing cover, respectively. Not explicitly shown in FIGS. 2A and 2B (but implied) is the seal (e.g., O-ring) disposed in the channel 208 and contacting the main housing 202 and housing cover 204. In this manner, a robust seal or closure is created which prevents intrusion of air or moisture into the interior space 206 of the enclosure 200. Furthermore, by hermetically sealing the enclosure 200, the interior space 206 of the enclosure will be at least somewhat insulated from the elevated temperatures to which the tracking apparatus is exposed during sterilization.

Figure 3A:
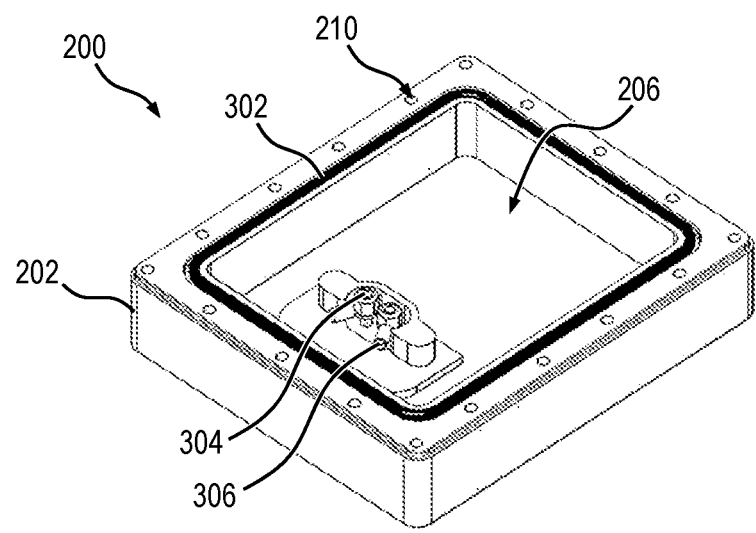
FIGS. 3A and 3B are perspective views depicting at least a portion of the interior space and a back surface, respectively, of the main housing of the exemplary enclosure shown in FIG. 2A, according to an embodiment of the invention.
Figure 3B:
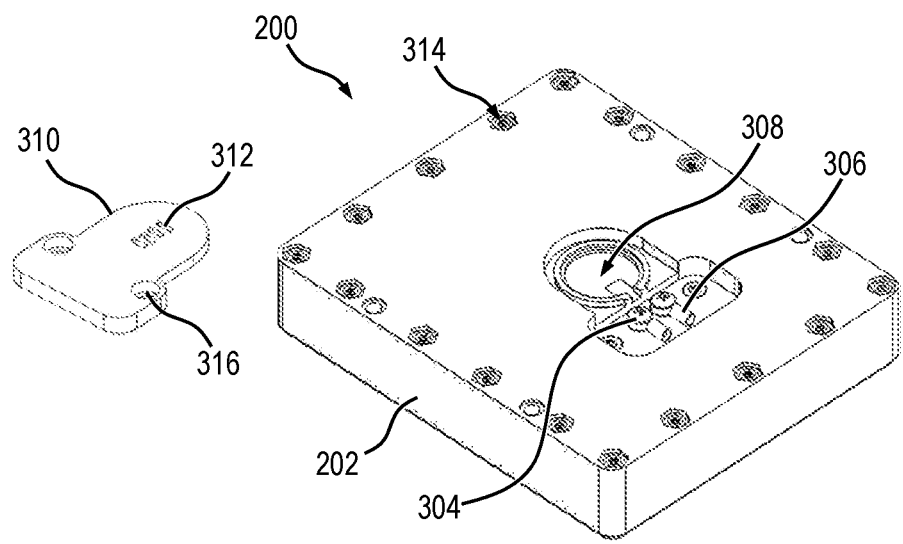

FIGS. 3A and 3B are perspective views depicting at least a portion of the interior space and back surface, respectively, of the main housing 202 of the exemplary enclosure 200 shown in FIG. 2A, according to an embodiment of the invention. With reference to FIG. 3A, the main housing 202 is shown with a sealing gasket 302, which may be an O-ring in one or more embodiments, disposed in a corresponding channel (e.g., 208 in FIG. 2A) adapted to receive the gasket. As previously stated in conjunction with FIGS. 2A and 2B, the underside of the housing cover (e.g., 204 in FIGS. 2A and 2B) preferably includes a rib that extends beyond the surface of a periphery of the cover and aligns with the sealing gasket 302 when the housing cover is placed over the main housing 202. The sealing gasket 302 is preferably flush (or even slightly recessed) with the upper surface of the channel in which in which it is disposed so that when the housing cover is placed on the main housing 202, the rib compresses the sealing gasket 302 into the corresponding channel thereby hermetically sealing the enclosure 200, as previously explained.

In one or more embodiments, the interior space 206 of the main housing 202 is adapted to contain the circuitry of the tracking apparatus, with the exception of the piezo element (e.g., 120 in FIG. 1). Rather, the piezo element is preferably disposed on an exterior surface of the enclosure 200. Accordingly, apertures (i.e., openings) are formed through a bottom of the main housing. Signal feedthroughs 304 are preferably passed through these apertures to facilitate electrical connection between the tracking apparatus circuitry, disposed in the interior space 206 of the main housing 202, and the piezo element, disposed on the exterior surface of the main housing. In one or more embodiments, each of the signal feedthroughs 304 comprises an electrically conductive fastener, which is preferably implemented using a metal bolt and nut, or other attachment means, and corresponding connection terminals 306 on both the interior (FIG. 3A) and exterior (FIG. 3B) of the main housing 202.

With reference now to FIG. 3B, the underside/exterior (back) surface of the main housing 202 of the enclosure 200 is shown, according to an embodiment of the invention. As apparent from FIG. 3B, the back surface of the main housing 202 includes a cavity 308 formed therein that is adapted to receive the piezo element. A depth of the cavity 308 is preferably greater than a cross-sectional thickness of the piezo element, such that when the piezo element is disposed within the cavity, it does not extend above an upper opening of the cavity. In this manner, when a piezo cover 310, configured in a shape of the cavity opening, is placed over the cavity 308 and secured in place, the piezo cover is preferably substantially planar with the back surface of the main housing 202.

Like the main housing 202, the piezo cover 310 comprises a thermoplastic polyetherimide high heat polymer or other material able to endure the high temperatures and pressures of sterilization, such as, but not limited to, ULTEM® 1000. It is to be understood, however, that embodiments of the invention are not limited to any specific material(s) used to form the piezo cover 310, and furthermore the piezo cover need not be formed of the same material used to form the main housing 202 or housing cover (204 in FIGS. 2A and 2B). In one or more embodiments, the piezo cover 310 includes one or more openings (i.e., apertures) 312 therein through which sound emanating from the piezo element may pass substantially unattenuated when the piezo element is disposed within the covered cavity 308.

With the piezo element disposed within the cavity 308, each electrical terminal of the piezo element is connected to a corresponding connection terminal 306 of the signal feedthrough 304. Similarly, on the other side of the feedthrough 304, on the interior space 206 of the main housing 202, the connection terminals 306 are electrically coupled to corresponding connection points on the tracking apparatus circuitry, such as the piezo driver (118 in FIG. 1), using wires or other connection means. In some embodiments, at least a portion of the circuitry of the tracking apparatus is disposed on a printed circuit board (PCB) or other substrate, and connection pads (not explicitly shown, but implied) on the PCB or substrate may be soldered directly to the connection terminals 306.

The signal feedthroughs 304 are preferably potted to prevent air and moisture intrusion into the interior space 206 of the enclosure 200 when the housing cover (204 in FIGS. 2A and 2B) is sealed to the main housing 202. With the signal feedthroughs potted, the piezo cover 310 need not be hermetically sealed with the main housing 202, which enables the piezo cover to provide openings 312 formed therein for superior sound emanation. This enables the tracking apparatus to advantageously audibly broadcast its location to a user, which is particularly helpful in locating a medical asset to which the tracking apparatus is attached when the medical asset resides in a large, noisy room of a medical facility, for example.

The main housing 202, in one or more embodiments, optionally includes countersunk cavities or inserts 314 that are adapted to receive either the head of a bolt or a nut, when using a bolt/nut attachment arrangement for securing the housing cover (e.g., 204 in FIG. 2) to the main housing 202. In some embodiments, the cavities 314 are hexagonally shaped and sized to match a shape of the nut, so that when a nut is placed in the cavity 314, it is prevented from turning as the bolt is tightened. Optionally, a depth of the cavity 314 is preferably configured so that it accommodates a thickness of the nut. In this manner, the nut will be substantially planar (i.e., flush) with the back surface of the main housing; that is, the nut used to attach the housing cover to the main housing will not protrude from the back surface of the main housing.

Similarly, the piezo cover 310 preferably includes one or more openings 316 through which a fastener or other attachment means passes for attaching the piezo cover to the back surface of the main housing 202. Optionally, in one or more embodiments, the openings 316 in the piezo cover 310, like the cavities 314 in the back surface of the main housing 202, are adapted to accommodate the head of a screw or other fastener so that it is planar (i.e., flush) with the back surface of the main housing when secured in place.

Figure 4:
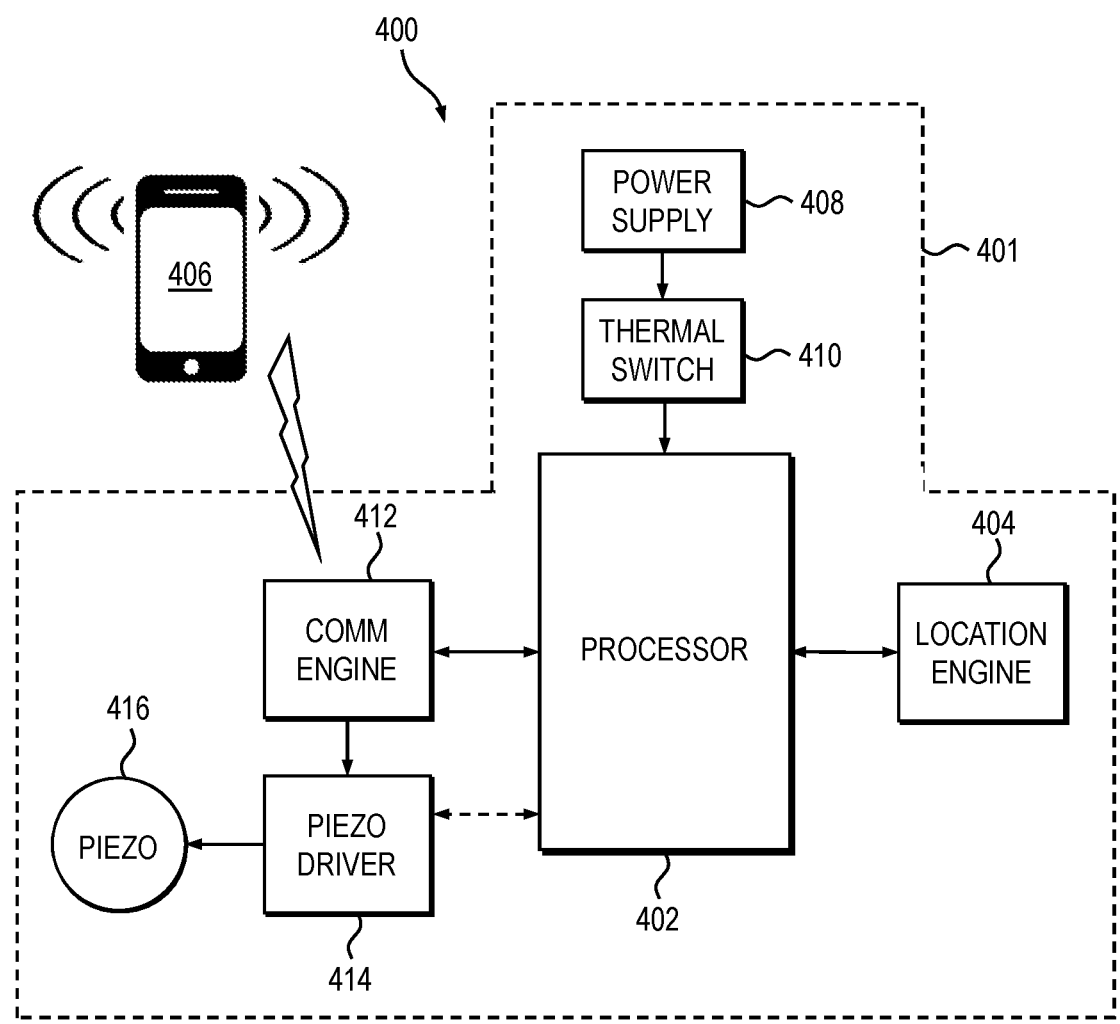
FIG. 4 is a block diagram depicting at least a portion of an exemplary system for tracking medical assets in a medical facility, according to an embodiment of the present invention.

In terms of operation, FIG. 4 is a block diagram conceptually depicting at least a portion of an exemplary system 400 for tracking medical assets in a medical facility, according to an embodiment of the invention. As shown in FIG. 4, a tracking apparatus 401 configured for tracking a location of a medical asset (e.g., surgical tray) in a medical facility or other space preferably includes at least one processor 402 operatively coupled with a location engine 404, which may comprise a GPS module and GPS antenna in one or more illustrative embodiments. Like the GPS module 104 and corresponding GPS antenna 110 depicted in FIG. 1, the location engine 404 is operative to supply geographic information (e.g., geographic coordinates) to the processor 402 regarding a location (e.g., absolute or relative position) of the tracking apparatus 401. The processor 402 then uses this location information to determine a position of the tracking apparatus 401 relative to a user, for example by comparing location information generated by a user's mobile device 406 with the geographic information obtained from the location engine 404 to calculate a geographical difference between the mobile device 406 and the tracking apparatus 401. In embodiments wherein absolute position information is not required, the location engine 404 may be omitted.

As previously described in conjunction with FIG. 1, the tracking apparatus 401 includes a power supply 408, which in a portable application typically comprises batteries, coupled with the processor 402 and other circuitry in the tracking apparatus via a thermally-responsive (thermal) switch 410. The thermal switch 410 functions to physically disconnect the power supply 408 from the entirety of the circuitry in the tracking apparatus 401 when a temperature in the tracking apparatus exceeds a prescribed threshold. In one or more embodiments, the prescribed temperature threshold is designed to be slightly less than a sterilization temperature, which is generally about 130° C. or higher. The thermal switch 410 reconnects the power supply 408 to the entirety of the circuitry in the tracking apparatus 401 when the temperature within the tracking apparatus falls to within an acceptable operating range.

The tracking apparatus 401 further includes a communications engine 412, which in one or more embodiments utilizes a BLE protocol, coupled with the processor 402. The communications engine 412 functions in a manner consistent with the BLE module 106 and corresponding BLE antenna 112 shown in FIG. 1. Specifically, the communications engine 412 preferably establishes a wireless personal area network for communicating with other Bluetooth-enabled devices using a BLE communications protocol. For example, the communications engine 412 preferably communicates with the user mobile device 406 through the wireless personal area network established by the communications engine. In one or more other embodiments, the communications engine 412 may include a cellular (e.g., 4G, 5G, etc.) transceiver to provide connectivity using a cellular infrastructure, or a transceiver configured to provide communications with a user device via another known communications protocol. In yet another embodiment, the communications engine 412 comprises an infrared transceiver for communicating with the user mobile device 406 via an optical communication link established therebetween.

In one or more embodiments, the user, via an application program executing on the user's mobile device 406, is able to send a request to the tracking apparatus 401 for initiating an audible alarm in the tracking apparatus to assist the user in locating the tracking apparatus in a large facility. The user request transmitted by the user's mobile device 406 is received by the communications engine 412 where, under control of the processor 402, an activation signal is sent to a piezo driver 414 for activating a piezo device 416 connected to the piezo driver. When activated, the piezo device 416 generates an audible alarm that can be heard by the user when the user is within a reasonable distance from the tracking apparatus 401. In alternative embodiments, the processor 402 is configured to generate the activation signal sent to the piezo driver 414 receipt of a user request, through an optional direct connection between the processor and piezo driver, for causing the piezo element 416 to produce an audible indication at periodic intervals, without user interaction. In this manner, the system 400 beneficially facilitates determining the location of a medical asset to which the tracking apparatus 401 is attached, even when the medical asset resides in a large, noisy room.

At least a portion of the apparatus of the present invention may be implemented in an integrated circuit. In forming integrated circuits, identical die are typically fabricated in a repeated pattern on a surface of a semiconductor wafer. Each die includes a device (or portion thereof) described herein, and may include other structures and/or circuits. The individual die are cut or diced from the wafer, then packaged as an integrated circuit. One skilled in the art would know how to dice wafers and package die to produce integrated circuits. Any of the exemplary circuits illustrated in the accompanying figures, or portions thereof, may be part of an integrated circuit. Integrated circuits so manufactured are considered part of this invention.

Those skilled in the art will appreciate that the exemplary structures described above can be distributed in raw form (i.e., a single wafer having multiple unpackaged chips), as bare dies, in packaged form, or incorporated as parts of intermediate products or end products that benefit from medical asset tracking apparatus and methods, in accordance with one or more embodiments of the invention.

An integrated circuit in accordance with aspects of the present disclosure can be employed in essentially any application and/or system where asset tracking in a facility is employed. Systems incorporating such integrated circuits are considered part of this invention. Given the teachings of the present disclosure provided herein, one of ordinary skill in the art will be able to contemplate other implementations and applications of embodiments of the invention.

The methodologies of embodiments of the present disclosure may be particularly well-suited for use in an electronic device or alternative system. Accordingly, embodiments of the present disclosure may take the form of an entirely hardware embodiment or an embodiment combining software and hardware aspects that may all generally be referred to herein as a "processor," "circuit," "module" or "system." Furthermore, embodiments of the present disclosure may take the form of a computer program product embodied in one or more computer readable medium(s) having computer readable program code stored thereon.

Any combination of one or more computer-usable or computer-readable medium(s) may be utilized. The computer-usable or computer-readable medium may be a computer-readable storage medium. A computer-readable storage medium may be, for example but not limited to, an electronic, magnetic, optical, electromagnetic, infrared, or semiconductor system, apparatus, device, or any suitable combination of the foregoing. More specific examples (a non-exhaustive list) of the computer-readable storage medium would include the following: a portable computer diskette, a hard disk, a random access memory (RAM), a read-only memory (ROM), an erasable programmable read-only memory (EPROM or flash memory), an optical fiber, a portable compact disc read-only memory (CD-ROM), an optical storage device, a magnetic storage device, or any suitable combination of the foregoing. In the context of this disclosure, a computer-readable storage medium may be any tangible medium that can contain or store a program for use by or in connection with an instruction execution system, apparatus or device.

Computer program code for carrying out operations of embodiments of the present disclosure may be written in any combination of one or more programming languages, including an object oriented programming language such as Java, Smalltalk, C++ or the like, and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present disclosure is described herein with reference to block diagrams of apparatus (systems) according to embodiments of the invention. It will be understood that each functional block of the block diagrams, or at least a portion thereof, and/or combinations of blocks in the block diagrams, may be implemented at least in part by computer program instructions. These computer program instructions may be stored in a computer-readable medium that can direct a computer or other programmable data processing apparatus or processor to function in a particular manner, such that the instructions stored in the computer-readable medium produce a specific article of manufacture including instruction means that implement the function/act specified in the block diagram block(s).

The illustrations of embodiments of the present invention described herein are intended to provide a general understanding of the various embodiments, and are not intended to serve as a complete description of all the elements and features of apparatus and systems that might make use of the circuits and techniques described herein. Many other embodiments will become apparent to those skilled in the art given the teachings herein; other embodiments are utilized and derived therefrom, such that structural and logical substitutions and changes can be made without departing from the scope of this disclosure. The drawings are also merely representational and are not drawn to scale. Accordingly, the specification and drawings are to be regarded in an illustrative rather than a restrictive sense.

Embodiments of the invention are referred to herein, individually and/or collectively, by the term "embodiment" merely for convenience and without intending to limit the scope of this application to any single embodiment or inventive concept if more than one is, in fact, shown. Thus, although specific embodiments have been illustrated and described herein, it should be understood that an arrangement achieving the same purpose can be substituted for the specific embodiment(s) shown; that is, this disclosure is intended to cover any and all adaptations or variations of various embodiments. Combinations of the above embodiments, and other embodiments not specifically described herein, will become apparent to those of skill in the art given the teachings herein.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. Terms such as "upper," "lower," "front" and "back," where used, indicate relative positioning of elements or structures to each other when such elements are oriented in a particular manner, as opposed to defining absolute positioning of the elements.

The corresponding structures, materials, acts, and equivalents of all means or step-plus-function elements in the claims below are intended to include any structure, material, or act for performing the function in combination with other claimed elements as specifically claimed. The description of the various embodiments has been presented for purposes of illustration and description, but is not intended to be exhaustive or limited to the forms disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the various embodiments with various modifications as are suited to the particular use contemplated.

The abstract is provided to comply with 37 C.F.R. § 1.72(b), which requires an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the appended claims reflect, inventive subject matter lies in less than all features of a single embodiment. Thus, the following claims are hereby incorporated into the Detailed Description, with each claim standing on its own as separately claimed subject matter.

Given the teachings of embodiments of the invention provided herein, one of ordinary skill in the art will be able to contemplate other implementations and applications of the techniques of embodiments of the invention. Although illustrative embodiments of the invention have been described herein with reference to the accompanying drawings, it is to be understood that embodiments of the invention are not limited to those precise embodiments, and that various other changes and modifications are made therein by one skilled in the art without departing from the scope of the appended claims.

What is claimed is:

1. An apparatus for tracking medical assets, the apparatus comprising:
   at least one processor;
   a power supply for providing power to an entirety of circuitry of the apparatus;
   a communications engine operatively coupled with the at least one processor, the communications engine configured to communicate with one or more mobile devices external to the apparatus;
   a piezoelectric element for generating an audible indication in response to an activation signal supplied thereto;
   a piezoelectric driver operatively coupled with the piezoelectric element and the processor, the piezoelectric driver configured to generate the activation signal supplied to the piezoelectric element; and
   a thermally-responsive, mechanically-actuated switch connected between the power supply and the entirety of circuitry of the apparatus, the thermally-responsive switch being configured to disconnect the power supply from the entirety of circuitry of the apparatus to thereby disable the apparatus when a temperature within the apparatus exceeds a prescribed threshold;
   wherein the piezoelectric element is disposed on an exterior surface of the apparatus, and wherein the apparatus is adapted to withstand elevated temperatures to which the apparatus is exposed during a sterilization process of a medical asset to which the apparatus is configured to be attached.

2. The apparatus of claim 1, further comprising at least two electrically conductive signal feedthroughs, the signal feedthroughs conveying electrical signals between the piezoelectric element, disposed on the exterior surface of the apparatus, and the piezoelectric driver, disposed in an interior space of the apparatus.

3. The apparatus of claim 2, wherein each of the signal feedthroughs comprises an electrically conductive fastener adapted to affix the piezoelectric element to the exterior surface of the apparatus.

4. The apparatus of claim 1, wherein the communications engine is configured to establish a wireless personal area network for communicating with the one or more mobile devices.

5. The apparatus of claim 1, further comprising a location engine operatively coupled with the at least one processor, the location engine being configured to supply geographic information to the processor regarding a location of the apparatus.

6. The apparatus of claim 5, wherein the location engine comprises a global positioning system (GPS) module and an antenna coupled with the GPS module.

7. The apparatus of claim 1, wherein the communications engine comprises at least one of a Bluetooth Low Energy (BLE) module, a cellular module, and an infrared transceiver.

8. The apparatus of claim 1, wherein the power supply comprises at least one battery, the apparatus further comprising a battery status circuit coupled with the battery and adapted to obtain information regarding an operational status of the battery and to provide said information to the at least one processor.

9. The apparatus of claim 8, wherein the power supply comprises a wireless charging circuit coupled with the at least one battery and configured to charge the at least battery from an external power source.

10. The apparatus of claim 1, further comprising a visual indicator operatively coupled with the at least one processor and adapted to provide a visual indication of the apparatus to a user in response to a control signal generated by the at least one processor.

11. The apparatus of claim 1, wherein the at least one processor is configured to modify at least one characteristic of the audible indication in response to one or more user-selectable parameters for uniquely identifying the apparatus to the user.

12. The apparatus of claim 1, wherein the activation signal is generated as a function of at least one of a user-initiated request signal received by the communications engine and a control signal generated by at least one processor.

13. A method for tracking a medical asset, the method comprising:
   attaching a tracking device to a medical asset being tracked, the tracking device including:
      at least one processor;
      a power supply for providing power to an entirety of circuitry of the tracking device;
      a communications engine operatively coupled with the processor, the communications engine configured to communicate with one or more mobile devices external to the tracking device;
a piezoelectric element disposed on an exterior surface of the tracking device for generating an audible indication in response to an activation signal supplied thereto; and
a piezoelectric driver operatively coupled with the piezoelectric element and the processor, the piezoelectric driver configured to generate the activation signal supplied to the piezoelectric element as a function of a control signal;

sending, by a user attempting to locate the medical asset, a request signal, whereby receiving the request signal by the communications engine causes the at least one processor to generate the control signal for activating the piezoelectric element to generate the audible indication for assisting the user in locating the medical asset; and disconnecting the power supply from the entirety of circuitry of the tracking device using a thermally-responsive, mechanically-actuated switch connected between the power supply and the entirety of circuitry of the tracking device, to thereby disable the tracking device when a temperature within the tracking device exceeds a prescribed threshold.

14. The method of claim 13, further comprising attaching the piezoelectric element to the exterior surface of the tracking device using at least two electrically conductive signal feedthroughs, the signal feedthroughs conveying electrical signals between the piezoelectric element, disposed on the exterior surface of the tracking device, and the piezoelectric driver, disposed in an interior space of the tracking device.

15. The method of claim 13, further comprising establishing, by the communications engine of the tracking device, a wireless network for facilitating communications between at least one mobile device of the user and the tracking device.

16. The method of claim 13, further comprising modifying, by the at least one processor, at least one characteristic of the audible indication in response to one or more user-selectable parameters for uniquely identifying the tracking device to the user.

17. The method of claim 13, wherein the tracking device includes a visual indicator operatively coupled with the at least one processor and adapted to provide a visual indication of the apparatus to the user, and wherein sending the request signal comprises activating, by the at least one processor, the visual indicator in response to the request signal.

18. The method of claim 13, wherein the tracking device includes a location engine operatively coupled with the at least one processor, the method further comprising sending, by the tracking device, geographical information generated by the location engine to the user to thereby assist the user in locating the medical asset.

* * * * *

UNITED STATES PATENT AND TRADEMARK OFFICE
CERTIFICATE OF CORRECTION

| | |
|---|---|
| PATENT NO. | : 11,273,005 B2 |
| APPLICATION NO. | : 16/789695 |
| DATED | : March 15, 2022 |
| INVENTOR(S) | : Beck et al. |

It is certified that error appears in the above-identified patent and that said Letters Patent is hereby corrected as shown below:

In the Specification

Column 1, Line 20: now reads "particular when the objects" should read --in particular when the objects--

Column 10, Line 20: now reads "in which in which it is" should read --in which it is--

Signed and Sealed this
Eighteenth Day of October, 2022

Katherine Kelly Vidal
*Director of the United States Patent and Trademark Office*